(12) United States Patent
Iwahama et al.

(10) Patent No.: US 8,680,267 B2
(45) Date of Patent: Mar. 25, 2014

(54) PROCESS FOR PRODUCING AMIDE OR LACTAM

(75) Inventors: Takahiro Iwahama, Himeji (JP); Tatsuya Nakano, Himeji (JP); Yasutaka Ishii, Takatsuki (JP)

(73) Assignee: Daicel Chemical Industries, Ltd., Osaka-Shi (JP)

( * ) Notice: Subject to any disclaimer, the term of this patent is extended or adjusted under 35 U.S.C. 154(b) by 319 days.

(21) Appl. No.: 12/997,287

(22) PCT Filed: Jun. 10, 2009

(86) PCT No.: PCT/JP2009/002627
§ 371 (c)(1),
(2), (4) Date: Dec. 10, 2010

(87) PCT Pub. No.: WO2009/150838
PCT Pub. Date: Dec. 17, 2009

(65) Prior Publication Data
US 2011/0092699 A1     Apr. 21, 2011

(30) Foreign Application Priority Data

Jun. 11, 2008   (JP) .................. 2008-152424

(51) Int. Cl.
*C07D 201/04* (2006.01)
*C07D 223/10* (2006.01)
*C07B 61/00* (2006.01)
*C07D 251/54* (2006.01)

(52) U.S. Cl.
USPC ........................ 540/464; 544/180; 544/214

(58) Field of Classification Search
USPC .................... 540/464; 544/180, 214
See application file for complete search history.

(56) References Cited

U.S. PATENT DOCUMENTS

| | | | |
|---|---|---|---|
| 3,825,532 A | 7/1974 | Kern et al. | |
| 5,254,684 A | 10/1993 | Izumi et al. | |
| 8,163,899 B2 * | 4/2012 | Ishihara et al. | 540/464 |
| 8,309,714 B2 * | 11/2012 | Kugimoto et al. | 540/464 |
| 2010/0029931 A1 | 2/2010 | Shibamoto et al. | |

FOREIGN PATENT DOCUMENTS

| | | |
|---|---|---|
| EP | 0515063 A1 | 11/1992 |
| GB | 1316740 | 5/1973 |
| JP | 46-23740 | 7/1971 |
| JP | 47-12780 | 6/1972 |
| JP | 51-34185 | 3/1976 |
| JP | 5-105654 A | 4/1993 |
| JP | 2003-529578 A | 10/2003 |
| JP | 2006-219470 A | 8/2006 |
| JP | 2008-156277 A | 7/2008 |
| WO | WO 01/74758 A1 | 10/2001 |
| WO | WO 2007/125002 A1 | 11/2007 |

OTHER PUBLICATIONS

De Luca, et al., "Beckmann Rearrangement of Oximes Under Very Mild Conditions", Journal of Organic Chemistry, vol. 67, 2002, pp. 6272-6274, XP003017098, (Published online Jul. 25, 2002).
Extended European Search Report, dated Apr. 27, 2012, for European Application No. 09762269.0.
Fernandez, et al., "The Role of Acids in the Beckmann Rearrangement of (—)-(1R,trans)-p-Menthan-3-one (E)-Oxime", Journal of Chemical Research (S), Issue 1, 1987, pp. 340-341, XP008110357.
Iranpoor, et al., "A Rapid and Facile Conversion of Primary Amides and Aldoximes to Nitriles and Ketoximes to Amides With Triphenylphosphine and N-Chlorosuccinimide", Synthetic Communications, vol. 32, No. 16, 2002, pp. 2535-2541, XP008124689.
International Search Report, dated Jul. 28, 2009, issued in corresponding International Application PCT/JP2009/002627.
Furuya et al., "Cyanuric Chloride as a Mild and Active Beckmann Rearrangement Catalyst", Journal of the American Chemical Society, vol. 127, No. 32, Jul. 23, 2005, pp. 11240-11241.
Hashimoto et al., "An Efficient Catalytic Method for the Beckmann Rearrangement of Ketoximes to Lactams by Cyanuric Chloride and Phosphazene Catalysts", Organic Process Research & Development, vol. 13, No. 3, Jan. 6, 2009, pp. 411-414.
Hashimoto et al., "Beckmann Rearrangement of Ketoximes to Lactams by Triphosphazene Catalyst", Journal of Organic Chemistry, vol. 73, No. 7, Mar. 5, 2008, pp. 2894-2897.
Ishii et al., "New Strategies for Sulfate-Free Synthesis of Lactams from Cycloalkanes Using NHPI as a Key Catalyst", Journal of Synthetic Organic Chemistry, vol. 66, No. 11, Nov. 2008, pp. 30-39.
Sato et al., "Homogeneous liquid-phase Beckmann rearrangement of oxime catalyzed by phosphorous pentaoxide and accelerated by fluorine-containing strong acid", Journal of Molecular Catalysis A: Chemical, vol. 149, Nos. 1-2, Dec. 15, 1999, pp. 25-32.

\* cited by examiner

*Primary Examiner* — Venkataraman Balasubramanian
(74) *Attorney, Agent, or Firm* — Birch, Stewart, Kolasch & Birch, LLP

(57) ABSTRACT

A process produces an amide or lactam by subjecting an oxime compound to rearrangement in a solvent in the presence of: at least one catalyst selected from the group consisting of an aromatic compound (A1) containing a leaving group bound to a carbon atom constituting the aromatic ring, the aromatic ring including, as a constitutive atom thereof, a heteroatom or including, as a constitutive atom thereof, a carbon atom bound to an electron-withdrawing group, and a compound (A2) containing a structure of Formula (1): -G-$L^A$ (1) wherein G represents P, N, S, B or Si atom; and $L^A$ represents a leaving group, wherein G is bound to one or more atoms or groups in addition to $L^A$; and a co-catalyst including a halogen-containing organic acid, to give the corresponding amide or lactam, wherein, when the aromatic compound (A1) alone is used as the catalyst, the solvent is at least one solvent selected typically from hydrocarbon solvents. The production process can yield amides or lactams simply in high yields without causing large amounts of by-products such as ammonium sulfate.

2 Claims, No Drawings

PROCESS FOR PRODUCING AMIDE OR LACTAM

TECHNICAL FIELD

The present invention relates to processes for producing amides or lactams that are useful, for example, as raw materials typically for pharmaceuticals, agricultural chemicals, dyestuffs and polyamides, and as solvents. More specifically, it relates to processes for producing the amides or lactams through rearrangement reactions of oxime compounds.

BACKGROUND ART

Techniques for producing amides or lactams from corresponding raw material oxime compounds through so-called "Beckmann rearrangement" are industrially very important. The production of these compounds has been performed using a process of allowing fuming sulfuric acid in a stoichiometric amount or more to act upon the raw material, but this process raises an issue of by-production of large amounts of ammonium sulfate to be treated.

To avoid this problem, there has been proposed a process of carrying out a reaction in a polar solvent by using a specific aromatic compound as a Beckmann rearrangement catalyst that places less load on the environment. In this process, the aromatic compound contains at least one carbon atom bound to a leaving group as an atom constituting its aromatic ring, contains a total of at least three atoms selected from heteroatoms and electron-withdrawing-group-containing carbon atoms as atoms constituting the aromatic ring, and two of the three atoms selected from heteroatoms and electron-withdrawing-group-containing carbon atoms are positioned each at the ortho position or para position of the carbon atom bound to the leaving group (see NPL 1 and PTL 1). This process, however, employs a polar solvent in the reaction, and the polar solvent should be removed prior to the separation of a reaction product lactam compound from the catalyst through an extraction operation using an organic solvent and water, because the polar solvent will inhibit the separation. This process is therefore disadvantageous in respect of energy and process from the viewpoint as a process for the industrial production of lactam compounds.

CITATION LIST

Patent Literature

PTL 1: Japanese Unexamined Patent Application Publication (JP-A) No. 2006-219470

Non Patent Literature

NPL 1: J. AM. CHEM. SOC. 2005, 127, 11240-11241

SUMMARY OF INVENTION

Technical Problem

Accordingly, an object of the present invention is to provide a process for producing an amide or lactam simply in a high yield while allowing a rearrangement reaction of an oxime compound to proceed without causing large amounts of by-products such as ammonium sulfate.

Another object of the present invention is to provide a process for producing an amide or lactam, which process does not need to use a polar solvent and thereby enables a simpler separation of a reaction product from a catalyst after the completion of the reaction.

Solution to Problem

After intensive investigations to solve the problems, the present inventors have found that the use of a compound having a specific structure as a constituent solves the problems. The present invention has been made based on these findings.

Specifically, the present invention provides a process for producing an amide or lactam. This process includes the step of subjecting an oxime compound to rearrangement in the presence of at least one catalyst and a co-catalyst in a solvent to yield the corresponding amide or lactam, in which the at least one catalyst is selected from the group consisting of an aromatic compound (A1) and a compound (A2), the aromatic compound (A1) contains an aromatic ring and a leaving group bound to a carbon atom constituting the aromatic ring, the aromatic ring includes, as a constitutive atom thereof, a heteroatom or including, as a constitutive atom thereof, a carbon atom bound to an electron-withdrawing group, the compound (A2) contains one or more structures represented by following Formula (1):

wherein G represents a P, N, S, B or Si atom; and $L^A$ represents a leaving group, wherein G is bound to one or more atoms or groups in addition to $L^A$, and the co-catalyst includes a halogen-containing organic acid, wherein, when the aromatic compound (A1) alone is used as the catalyst, the solvent is at least one solvent selected from the group consisting of hydrocarbon solvents, ether solvents, halogenated hydrocarbon solvents and ketone solvents.

The aromatic compound (A1) is preferably an aromatic compound containing, as a constituent of the aromatic ring, one or more structures represented by following Formula (2):

[Chem. 1]

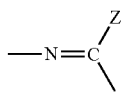

wherein Z represents a halogen atom or an —OR group, wherein R represents an organic group.

The leaving group $L^A$ in Formula (1) in the compound (A2) is preferably a halogen atom.

Advantageous Effects of Invention

According to the present invention, amides or lactams can be produced simply in high yields, because rearrangement reactions of oximes can be carried out without causing large amounts of by-products such as ammonium sulfate, and whereby problems occurring in customary processes for producing amides or lactams, such as removal and disposal of by-products, can be avoided. In addition, the process according to the present invention does not need to use a polar solvent and thereby allows simple separation between a reaction product and the used catalysts after the completion of the reaction typically through an extraction operation with water. This allows corresponding amides or lactams to be produced from oxime compounds industrially efficiently at low cost.

DESCRIPTION OF EMBODIMENTS

The production process according to the present invention carries out rearrangement of an oxime compound into a corresponding amide or lactam by the catalysis of a co-catalyst including a halogen-containing organic acid and of at least one catalyst selected from the group consisting of an aromatic compound (A1) and a compound (A2), in which the aromatic compound (A1) contains an aromatic ring and a leaving group bound to a carbon atom constituting the aromatic ring, the aromatic ring including, as a constitutive atom thereof, a heteroatom or including, as a constitutive atom thereof, a carbon atom bound to an electron-withdrawing group, and the compound (A2) contains a structure represented by Formula (1).

[Aromatic Compounds (A1)]

In the aromatic compound (A1), examples of the aromatic ring include aromatic hydrocarbon rings and aromatic heterocyclic rings. Exemplary aromatic hydrocarbon rings include monocyclic aromatic hydrocarbon rings such as benzene ring; and polycyclic aromatic hydrocarbon rings including fused rings such as naphthalene ring, anthracene ring, fluorene ring and phenanthrene ring, as well as biphenyl ring and terphenyl ring. Exemplary aromatic heterocyclic rings include five-membered aromatic heterocyclic rings such as pyrrole ring, furan ring, thiophene ring, imidazole ring, pyrazole ring, triazole ring, tetrazole ring, oxazole ring, isoxazole ring and thiazole ring; six-membered aromatic heterocyclic rings such as pyridine ring, pyrazine ring, pyrimidine ring, pyridazine ring and triazine ring; and fused heterocyclic rings such as indole ring, benzoimidazole ring, benzotriazole ring, quinoline ring, bipyridyl ring and phenanthroline ring. Of such aromatic hydrocarbon rings, benzene ring is especially preferred. Of such aromatic heterocyclic rings, nitrogen-containing heterocyclic rings such as pyridine ring and triazine ring are especially preferred.

The leaving group bound to a carbon atom constituting the aromatic ring is not especially limited, as long as being a group capable of leaving, and examples of such leaving groups include halogen atoms (fluorine atom, chlorine atom, bromine atom and iodine atom), diazonium group, sulfonyl halide groups (such as sulfonyl chloride group), carbonyl halide groups (such as carbonyl chloride group) and —OR groups, wherein R represents an organic group.

Exemplary organic groups as R include sulfonyl groups (e.g., arylsulfonyl groups such as benzenesulfonyl group, p-toluenesulfonyl group and naphthalenesulfonyl group; and alkanesulfonyl groups such as methanesulfonyl group, trifluoromethanesulfonyl group and ethanesulfonyl group), haloalkyl groups [e.g., haloalkyl groups having 1 to about 17 carbon atoms (of which those having 1 to about 10 carbon atoms are preferred), including fluorinated alkyl groups such as difluoromethyl group, trifluoromethyl group, tetrafluoroethyl group, pentafluoroethyl group and fluorine-containing branched-chain aliphatic groups represented by following Formula (3); and chlorinated alkyl groups such as trichloromethyl group], alkylideneamino groups represented by following Formula (4a) and cycloalkylideneamino groups represented by following Formula (4b) (of which an alkylideneamino group or cycloalkylideneamino group corresponding to the raw material oxime compound is preferred).

[Chem. 2]

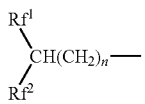

(3)

[Chem. 3]

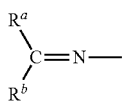

(4a)

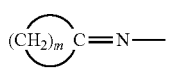

(5a)

In the fluorine-containing branched-chain aliphatic groups represented by Formula (3), $Rf^1$ and $Rf^2$ are the same as or different from each other and each represent a perfluoroalkyl group having 1 to 8 carbon atoms; and "n" denotes an integer of 0 to 10. Exemplary perfluoroalkyl groups having 1 to 8 carbon atoms include trifluoromethyl group, pentafluoroethyl group and heptafluoropropyl group. Typical examples of the fluorine-containing branched-chain aliphatic groups represented by Formula (3) include hexafluoroisopropyl group.

In Formula (4a), $R^a$ and $R^b$ each independently represent an organic group, wherein one of $R^a$ and $R^b$ may be a hydrogen atom. The organic groups as $R^a$ and $R^b$ are as with organic groups as $R^a$ and $R^b$ in the oxime compound mentioned below. In Formula (5a), "m" denotes an integer of 2 or more. Typical examples of the groups represented by Formula (4a) include a group in which $R^a$ is methyl group and $R^b$ is phenyl group; a group in which $R^a$ is methyl group and $R^b$ is p-methoxyphenyl group; a group in which $R^a$ is methyl group and $R^b$ is o-methoxyphenyl group; and a group in which $R^a$ is methyl group and $R^b$ is p-fluorophenyl group. Typical examples of the groups represented by Formula (5a) include cyclopentylideneamino group, cyclohexylideneamino group, cyclooctylideneamino group, cyclodecylideneamino group, cyclododecylideneamino group and cyclopentadecylideneamino group.

Examples of the heteroatom as a constitutive atom of the aromatic ring include nitrogen atom, oxygen atom, sulfur atom and silicon atom. Of these, nitrogen atom is preferred. When the aromatic ring contains a carbon atom bound to an electron-withdrawing group as a constitutive atom thereof, examples of the electron-withdrawing group include, but are not especially limited to, cyano group; halomethyl groups such as trifluoromethyl group and trichloromethyl group; nitro group; carbonyl halide groups; acyl groups; and sulfonyl groups. The aromatic compound (A1) preferably contains, as constitutive atoms of the aromatic ring, a total of three or more atoms selected from the group consisting of heteroatoms and electron-withdrawing-group-bound carbon atoms. Two of the heteroatoms and electron-withdrawing-group-bound carbon atoms are preferably positioned each at the ortho position or para position of the carbon atom bound to the leaving group.

Preferred aromatic compounds (A1) include aromatic compounds containing one or more structures represented by Formula (2) as a constituent of the aromatic ring. In Formula (2), Z represents a halogen atom or an —OR group, wherein R represents an organic group. Exemplary halogen atoms as Z include fluorine atom, chlorine atom, bromine atom and iodine atom. Of these, chlorine atom is preferred. Exemplary organic groups as R are as above.

Exemplary aromatic compounds containing one or more structures represented by Formula (2) as a constituent of the aromatic ring include triazine derivatives represented by following Formula (2a), pyrazine derivatives represented by following Formula (2b), pyrimidine derivatives represented by following Formula (2c), pyridazine derivatives represented by following Formula (2d) and pyridine derivatives represented by following Formula (2e):

[Chem. 4]

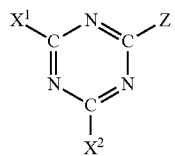
(2a)

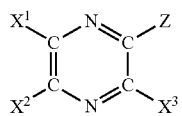
(2b)

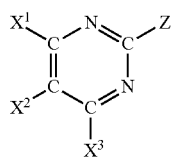
(2c)

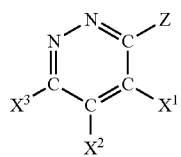
(2d)

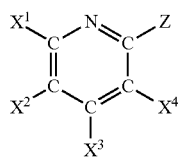
(2e)

wherein Z represents a halogen atom or an —OR group, wherein R represents an organic group; and $X^1$, $X^2$, $X^3$ and $X^4$ are the same as or different from each other and each represent a hydrogen atom, halogen atom, alkyl group, haloalkyl group (such as trifluoromethyl group, difluoromethyl group or trichloromethyl group), aryl group, cycloalkyl group, hydroxyl group, alkoxy group, aryloxy group, haloalkoxy group, mercapto group, carboxyl group, substituted oxycarbonyl group, formyl group, acyl group, acyloxy group, nitro group, sulfo group, cyano group, amino group, oxyamino group or another organic group, in which at least two of $X^1$, $X^2$, $X^3$ and $X^4$ may be bound to each other to form an aromatic or nonaromatic ring with atoms constituting the ring in the formula.

Exemplary haloalkoxy groups as $X^1$, $X^2$, $X^3$ and $X^4$ include haloalkoxy groups having 1 to about 17 carbon atoms, such as difluoromethyloxy group, trifluoromethyloxy group, tetrafluoroethyloxy group, pentafluoroethyloxy group and hexafluoroisopropyloxy group (2,2,2-trifluoro-1-trifluoromethylethoxy group), of which those having 1 to about 10 carbon atoms are preferred. Of such haloalkoxy groups, fluorinated alkyloxy groups are especially preferred. Exemplary other organic groups as $X^1$, $X^2$, $X^3$ and $X^4$ include alkylideneamino groups and cycloalkylideneamino groups. $X^1$, $X^2$, $X^3$ and $X^4$ are preferably leaving groups. Z herein may be a leaving group other than the halogen atom or —OR group.

The substituents $X^1$, $X^2$, $X^3$ and $X^4$ in the compounds represented by Formulae (2a), (2b), (2c), (2d) and (2e) can each be a group as with Z, i.e., they can be groups selected from halogen atoms and —OR groups. Specifically, a triazine derivative represented by Formula (2a), when $X^1$ and $X^2$ are independently groups selected from halogen atoms and —OR groups, be an aromatic compound containing three structures represented by Formula (2) per one molecule. Likewise, a pyrazine derivative represented by Formula (2b), a pyrimidine derivative represented by Formula (2c) and a pyridazine derivative represented by Formula (2d), when $X^3$ is a group selected from a halogen atom and an —OR group, be aromatic compounds each containing two structures represented by Formula (2) per one molecule.

Specifically, concrete examples of the triazine derivatives represented by Formula (2a) include triazine derivatives having one or more halogen atoms (of which chlorine atoms are preferred) as substituents, such as 2-chloro-1,3,5-triazine, 2,4-dichloro-1,3,5-triazine, 2,4,6-trichloro-1,3,5-triazine (cyanuric chloride), 2-chloro-4,6-dihydroxy-1,3,5-triazine, 2-chloro-4,6-dinitro-1,3,5-triazine, 2-chloro-4-nitro-1,3,5-triazine and 2-chloro-4,6-dioxymethyl-1,3,5-triazine; triazine derivatives having one or more haloalkoxy groups as substituents, such as 2-hexafluoroisopropyloxy-1,3,5-triazine, 2,4-bis(hexafluoroisopropyloxy)-1,3,5-triazine and 2,4,6-tris(hexafluoroisopropyloxy)-1,3,5-triazine; triazine derivatives having one or more cycloalkylideneaminooxy groups as substituents, such as 2-cyclododecylideneaminooxy-1,3,5-triazine, 2,4-bis(cyclododecylideneaminooxy)-1,3,5-triazine and 2,4,6-tris(cyclododecylideneaminooxy)-1,3,5-triazine; triazine derivatives having one or more halogen atoms and one or more haloalkoxy groups as substituents, such as 2-chloro-4,6-bis(hexafluoroisopropyloxy)-1,3,5-triazine and 2,4-dichloro-6-(hexafluoroisopropyloxy)-1,3,5-triazine; triazine derivatives having one or more halogen atoms and one or more cycloalkylideneaminooxy groups as substituents, such as 2-chloro-4-cyclododecylideneaminooxy-1,3,5-triazine; triazine derivatives having one or more cycloalkylideneaminooxy groups and one or more haloalkoxy groups as substituents, such as 2-cyclododecylideneaminooxy-4,6-bis(hexafluoroisopropyloxy)-1,3,5-triazine; and triazine derivatives having a halogen atom, a haloalkoxy group and a cycloalkylideneamino group as substituents, such as 2-chloro-4-(hexafluoroisopropyloxy)-6-cyclododecylideneaminooxy-1,3,5-triazine.

Specific examples of the pyrazine derivatives represented by Formula (2b) include pyrazine derivatives having one or more halogen atoms as substituents, such as 2-chloropyrazine, 2,3-dichloropyrazine and 2-chloro-3,5-dinitropyrazine; pyrazine derivatives having one or more haloalkoxy groups as substituents, such as 2-(hexafluoroisopropyloxy)pyrazine; and pyrazine derivatives having one or more cycloalkylideneaminooxy groups as substituents, such as 2-cyclododecylideneaminooxypyrazine.

Specific examples of pyrimidine derivatives represented by Formula (2c) include pyrimidine derivatives having one or more halogen atoms as substituents, such as 2,4-dichloropyrimidine, 2,4,6-trichloropyrimidine, 4,6-dichloro-5-nitropyrimidine and 2,4-dichloro-6-nitropyrimidine; pyrimidine derivatives having one or more haloalkoxy groups as substituents, such as 2,4-bis(hexafluoroisopropyloxy)pyrimidine; and pyrimidine derivatives having one or more cycloalkylideneaminooxy groups as substituents, such as 2,4-dicyclododecylideneaminooxypyrimidine.

Specific examples of the pyridazine derivatives represented by Formula (2d) include pyridazine derivatives having one or more halogen atoms as substituents, such as 3-chloropyridazine and 3,6-dichloropyridazine; pyridazine derivatives having one or more haloalkoxy groups as substituents, such as 3-hexafluoroisopropyloxypyridazine; and pyridazine derivatives having one or more cycloalkylideneaminooxy groups as substituents, such as 3-cyclododecylideneaminooxypyridazine.

Specific examples of the pyridine derivatives represented by Formula (2e) include pyridine derivatives having one or more halogen atoms as substituents, such as 2-chloro-3,5-dinitropyridine, 2,4,6-trichloropyridine and 2-chloropyridine; pyridine derivatives having one or more haloalkoxy groups as substituents, such as 2-hexafluoroisopropyloxypyridine; and pyridine derivatives having one or more cycloalkylideneaminooxy groups as substituents, such as 2-cyclododecylideneaminooxypyridine.

Of these, triazine derivatives represented by Formula (2a) are advantageously usable, of which 2,4,6-trichloro-1,3,5-triazine, 2,4,6-tris(hexafluoroisopropyloxy)-1,3,5-triazine and/or 2,4,6-tris(cyclododecylideneaminooxy)-1,3,5-triazine is especially advantageously usable.

The aromatic compound containing a structure represented by Formula (2) as a ring constituent may be a compound having a nitrogen-containing fused heterocyclic ring skeleton such as quinoline, isoquinoline, quinazoline, quinoxaline, phthalazine, purine, pteridine, phenanthridine or phenanthroline.

When the aromatic compound containing a structure represented by Formula (2) as a ring constituent is a compound having an —OR group as Z, the aromatic compound may be previously prepared before use in the reaction, but such aromatic compound having an —OR group as Z can also be formed within the reaction system, by incorporating a corresponding compound having a halogen atom as Z and a compound capable of generating an RO⁻ ion into the reaction system for the production of a lactam compound, and whereby allowing a substitution reaction between the halogen atom and —OR group to proceed in the reaction system. Though not especially limited, the compound capable of generating an RO⁻ ion is often the oxime compound used as a raw material. Specifically, embodiments of the present invention in which Z is an —OR group include an embodiment in which an aromatic compound containing, as a ring constituent, a structure represented by Formula (2) wherein Z is a halogen atom is used, and this aromatic compound reacts with a raw material oxime compound to give an aromatic compound having a group corresponding to the oxime compound, except for removing a hydrogen atom therefrom, (e.g., cycloalkylideneaminooxy group) as a substituent.

Of aromatic compounds (A1), exemplary aromatic compounds other than the aromatic compounds containing a structure represented by Formula (2) as a ring constituent include benzene derivatives such as 4-chloro-3,5-dinitrobenzonitrile and picryl chloride.

[Compounds (A2) Containing Structure Represented by Formula (1)]

In Formula (1), G represents a P, N, S, B or Si atom; and $L^A$ represents a leaving group. The leaving group as $L^A$ can be any of common leaving functional groups (of which a group that is capable of leaving as $L^A$-His preferred), and examples thereof include halogen atoms (fluorine atom, chlorine atom, bromine atom and iodine atom), —OR' groups (wherein R' represents an organic group), carboxyl group, amino group and sulfonyloxy groups. Among them, a halogen atom is preferably used as $L^A$. Though not especially limited, preferred examples of the organic group as R' include the alkylideneamino groups represented by Formula (4a) and the cycloalkylideneamino groups represented by Formula (5a) (of which an alkylideneamino group or cycloalkylideneamino group corresponding to the raw material oxime compound is preferred), alkyl groups and haloalkyl groups.

Exemplary alkyl groups as R' include straight- or branched-chain alkyl groups having 1 to 10 carbon atoms, such as methyl, ethyl, propyl, isopropyl, butyl, isobutyl, s-butyl, t-butyl, pentyl and hexyl. Exemplary haloalkyl groups as R' include groups corresponding to the alkyl groups, except for being substituted with one or more halogen atoms such as fluorine, chlorine, bromine and iodine. Such haloalkyl groups may each have one or more halogenated aryl groups as substituents. Of haloalkyl groups, fluorinated alkyl groups having one or more fluorine atoms as substituents are preferred, of which more preferred are fluorine-containing branched-chain aliphatic groups represented by following Formula (d); fluorine-containing straight-chain aliphatic groups represented by Formula (e); and fluorine-containing aliphatic chain groups having a fluorophenyl group bound thereto, such as a group represented by Formula (f). When the group represented by R' is a fluorinated alkyl group, the fluorinated alkyl group is often a group corresponding to a fluorine-containing alcohol mentioned later:

[Chem. 5]

$$\begin{array}{c}Rf^1\\ \phantom{Rf^1}\diagdown\\ \phantom{Rf^1}CH(CH_2)_n-\!\!\!-\\ \phantom{Rf^1}\diagup\\ Rf^2\end{array} \quad (d)$$

$$CF_3(CF_2)_nCH_2-\!\!\!- \quad (e)$$

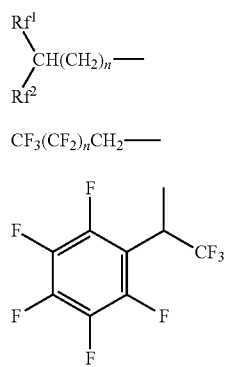

(f)

wherein $Rf^1$ and $Rf^2$ are the same as or different from each other and each represent a perfluoroalkyl group having 1 to 8 carbon atoms; and "n" denotes an integer of 0 to 10.

Exemplary perfluoroalkyl groups having 1 to 8 carbon atoms are as above.

The compound containing one or more structures represented by Formula (1) is not especially limited, as long as being a compound containing one or more of the structure per molecule, and may be a cyclic compound or acyclic compound.

Exemplary compounds containing one or more structures represented by Formula (1) for use herein include phosphazene compounds (phosphazene derivatives) represented by following Formula (1a), phosphoric ester compounds (phosphoric ester derivatives) represented by Formula (1b), phosphine compounds (phosphine derivatives) represented by Formula (1c), imide compounds (imide derivatives) represented by Formula (1d), sulfonyl or sulfinyl compounds (sulfonyl or sulfinyl derivatives) represented by Formula (1e), silane compounds (silane derivatives) represented by Formula (1f), and cyclic compounds represented by Formula (1g) and containing silicon atoms as ring constituents:

[Chem. 6]

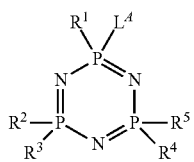
(1a)

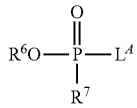
(1b)

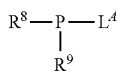
(1c)

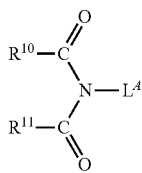
(1d)

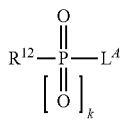
(1e)

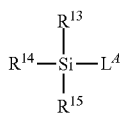
(1f)

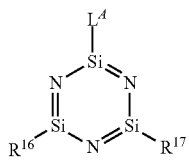
(1g)

wherein $L^A$ is as defined above; "k" denotes 0 or 1; and $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ are the same as or different from one another and each represent a hydrogen atom, halogen atom, alkyl group, haloalkyl group, aryl group, aralkyl group, cycloalkyl group, hydroxyl group, alkoxy group, aryloxy group, haloalkoxy group, mercapto group, carboxyl group, substituted oxycarbonyl group, acyl group, acyloxy group, nitro group, sulfo group, cyano group, amino group, oxyamino group, or another organic group. In Formula (1a), $R^2$ and $R^3$ may be bound to each other to form a ring with the adjacent phosphorus atom; and $R^4$ and $R^5$ may be bound to each other to form a ring with the adjacent phosphorus atom. In Formula (1b), $R^6$ and $R^7$ may be bound to each other to form a ring with the adjacent oxygen atom and phosphorus atom. In Formula (1c), $R^8$ and $R^9$ may be bound to each other to form a ring with the adjacent phosphorus atom. In Formula (1d), $R^{18}$ and $R^{11}$ may be bound to each other to form a ring with the adjacent two carbon atoms and nitrogen atom. In Formula (1f), at least two of $R^{13}$, $R^{14}$ and $R^{15}$ may be bound to each other to form a ring with the adjacent silicon atom.

As $R^1$ to $R^{17}$, exemplary halogen atoms include iodine, bromine, chlorine and fluorine atoms. Exemplary alkyl groups include straight- or branched-chain alkyl groups having 1 to about 30 carbon atoms, such as methyl, ethyl, propyl, isopropyl, butyl, isobutyl, s-butyl, t-butyl, hexyl, decyl, dodecyl, tetradecyl and hexadecyl groups, of which those having 1 to 20 carbon atoms are preferred, and those having 1 to 6 carbon atoms are more preferred. Exemplary haloalkyl groups include groups corresponding to the alkyl groups, except for being substituted with one or more halogen atoms such as fluorine, chlorine, bromine and iodine.

Exemplary aryl groups include phenyl, tolyl, xylyl and naphthyl groups; exemplary aralkyl groups include benzyl, 2-phenylethyl, 1-phenylethyl and trityl groups; and exemplary cycloalkyl groups include cyclopentyl and cyclohexyl groups. Exemplary alkoxy groups include alkoxy groups having 1 to about 30 carbon atoms, such as methoxy, ethoxy, isopropoxy, butoxy, t-butoxy, hexyloxy, octyloxy, decyloxy, dodecyloxy, tetradecyloxy and octadecyloxy groups, of which those having 1 to 20 carbon atoms are preferred, and those having 1 to 6 carbon atoms are more preferred. Exemplary aryloxy groups include phenyloxy group.

Exemplary haloalkoxy groups include groups corresponding to fluorine-containing branched-chain aliphatic alcohols, except for removing a hydrogen atom therefrom [groups corresponding to the fluorine-containing branched-chain aliphatic groups represented by Formula (d), except with an oxygen atom bound thereto], such as hexafluoroisopropyloxy group (2,2,2-trifluoro-1-trifluoromethylethoxy group); groups corresponding to fluorine-containing straight-chain aliphatic alcohols (fluorine-containing primary alcohols), except for removing a hydrogen atom therefrom [groups corresponding to the fluorine-containing straight-chain aliphatic groups represented by Formula (e), except with an oxygen atom bound thereto]; and groups corresponding to fluorine-containing aliphatic chain groups bound with a fluorophenyl group, except with an oxygen atom bound thereto, such as a group corresponding to the group represented by Formula (f), except with an oxygen atom bound thereto.

Exemplary substituted oxycarbonyl groups include alkoxy-carbonyl groups whose alkoxy moiety having 1 to 30 carbon atoms, such as methoxycarbonyl, ethoxycarbonyl, isopropoxycarbonyl, butoxycarbonyl, t-butoxycarbonyl, hexyloxycarbonyl, decyloxycarbonyl and hexadecyloxycarbonyl groups, of which alkoxy-carbonyl groups whose alkoxy moiety having 1 to 20 carbon atoms are preferred, and alkoxy-carbonyl groups whose alkoxy moiety having 1 to 6 carbon atoms are more preferred; cycloalkyloxycarbonyl groups such as cyclopentyloxycarbonyl and cyclohexyloxycarbonyl groups, of which cycloalkyloxycarbonyl groups having 3 to 20 members are preferred, and cycloalkyloxycarbonyl groups having 3 to 15 members are more preferred; aryloxycarbonyl groups such as phenyloxycarbonyl and naphthyloxycarbonyl groups, of which aryloxy-carbonyl groups whose aryloxy moiety having 6 to 20 carbon atoms are preferred; and aralkyloxycarbonyl groups such as benzyloxycarbonyl group, of which aralkyloxy-carbonyl groups whose aralkyloxy moiety having 7 to 21 carbon atoms are preferred.

Exemplary acyl groups include aliphatic saturated or unsaturated acyl groups including aliphatic acyl groups having 1 to 30 carbon atoms, such as formyl, acetyl, propionyl, butyryl, isobutyryl, valeryl, pivaloyl, hexanoyl, octanoyl, decanoyl, lauroyl, myristoyl, palmitoyl and stearoyl groups, of which aliphatic acyl groups having 1 to 20 carbon atoms are preferred, and aliphatic acyl groups having 1 to 6 carbon atoms are more preferred; acetoacetyl group; alicyclic acyl groups including cycloalkanecarbonyl groups such as cyclopentanecarbonyl and cyclohexanecarbonyl groups; and aromatic acyl groups such as benzoyl and naphthoyl groups.

Exemplary acyloxy groups include aliphatic saturated or unsaturated acyloxy groups including aliphatic acyloxy groups having 1 to 30 carbon atoms, such as formyloxy, acetyloxy, propionyloxy, butyryloxy, isobutyryloxy, valeryloxy, pivaloyloxy, hexanoyloxy, octanoyloxy, decanoyloxy, lauroyloxy, myristoyloxy, palmitoyloxy and stearoyloxy groups, of which aliphatic acyloxy groups having 1 to 20 carbon atoms are preferred; acetoacetyloxy group; alicyclic acyloxy groups including cycloalkanecarbonyloxy groups such as cyclopentanecarbonyloxy and cyclohexanecarbonyloxy groups; and aromatic acyloxy groups such as benzoyloxy and naphthoyloxy groups. Examples of the other organic group include the groups represented by Formula (4a) or (5a).

Though not especially limited, the rings formed by the pair or $R^2$ and $R^3$ and the pair of $R^4$ and $R^5$, respectively, with the adjacent phosphorus atom, the ring formed by $R^6$ and $R^7$ with the adjacent oxygen atom and phosphorus atom, the ring formed by $R^8$ and $R^9$ with the adjacent phosphorus atom, the ring formed by $R^{10}$ and $R^{11}$ with the adjacent two carbon atoms and nitrogen atom, and the ring formed by at least two of $R^{13}$, $R^{14}$, and $R^{15}$ with the adjacent silicon atom are generally heterocyclic rings each having 3 to about 12 members. These rings may each have one or more substituents bound thereto. These rings may have one or more other rings fused therewith. Exemplary substituents herein include alkyl groups, haloalkyl groups, hydroxyl group, alkoxy groups, carboxyl group, substituted oxycarbonyl groups, acyl groups, acyloxy groups, nitro group, cyano group, amino groups, and halogen atoms. Exemplary rings to be fused include aromatic hydrocarbon rings such as benzene ring; aromatic heterocyclic rings such pyridine ring; nonaromatic hydrocarbon rings (aliphatic rings) such as cyclohexane ring; and nonaromatic heterocyclic rings such as tetrahydrofuran ring.

In the compounds represented by Formulae (1a) to (1g), the groups $R^1$ to $R^{17}$ can be leaving groups as with $L^A$, of which halogen atoms and —OR' groups (wherein R' represents an organic group) are preferred. A phosphazene compound represented by Formula (1a), when at least $R^2$ and $R^4$ are leaving groups as with $L^A$, be a cyclic compound having three structures represented by Formula (1) per one molecule. Likewise, a cyclic compound represented by Formula (1g) and containing silicon atoms as ring constituents, when $R^{16}$ and $R^{17}$ are leaving groups as with $L^A$, be a cyclic compound having three structures represented by Formula (1) per one molecule.

In Formula (1b), $R^6$ is especially preferably an alkyl group, haloalkyl group, aryl group, aralkyl group or cycloalkyl group; and $R^7$ is preferably a leaving group as with $L^A$ [of which a halogen atom or —OR' group (wherein R' represents an organic group) is preferred], or an —OR$^6$ group. In Formula (1c), $R^8$ and $R^9$ are each especially preferably an alkyl group, a haloalkyl group, an aryl group, an aralkyl group, a cycloalkyl group, or a leaving group as with $L^A$ [of which a halogen atom or —OR' group (wherein R' represents an organic group) is preferred].

In Formula (1d), it is especially preferred that $R^{10}$ and $R^{11}$ are bound to each other to form a ring with the adjacent two carbon atoms and nitrogen atom. The ring may have one or more substituents bound thereto and may have one or more other rings fused therewith. In Formula (1e), $R^{12}$ is especially preferably an alkyl group, a haloalkyl group, an aryl group, an aralkyl group, a cycloalkyl group, or a leaving group as with $L^A$ [of which a halogen atom or —OR' group (wherein R' represents an organic group) is preferred]. In Formula (1f), $R^{13}$, $R^{14}$ and $R^{15}$ are each especially preferably an alkyl group, a haloalkyl group, an aryl group, an aralkyl group, a cycloalkyl group, or a leaving group as with $L^A$ [of which a halogen atom or —OR' group (wherein R' represents an organic group) is preferred].

Specific examples of the phosphazene compounds represented by Formula (1a) include halophosphazene derivatives such as hexachlorophosphazene (compound wherein $L^A$, $R^1$, $R^2$, $R^3$, $R^4$ and $R^5$ are each chlorine (Cl)), hexafluorophosphazene (compound wherein $L^A$, $R^1$, $R^2$, $R^3$, $R^4$ and $R^5$ are each fluorine (F)) and hexabromophosphazene (compound wherein $L^A$, $R^1$, $R^2$, $R^3$, $R^4$ and $R^5$ are each bromine (Br)); and compounds represented by following Formula (1a-1):

[Chem. 7]

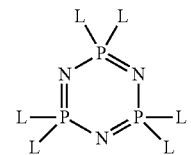

(1a-1)

wherein Ls each represent a group represented by following Formula (a), (b) or (c):

[Chem. 8]

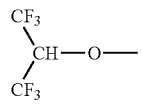

(a)

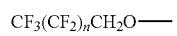

(b)

$CF_3(CF_2)_nCH_2O$——

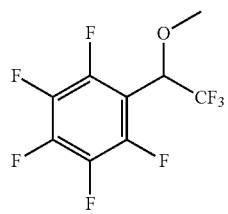

(c)

wherein "n" in Formula (b) denotes an integer of 0 to 10.

Exemplary phosphoric ester compounds represented by Formula (1b) include dimethyl chlorophosphate, diethyl chlorophosphate, 2-chloro-1,3,2-dioxaphospholane-2-oxide, methyl dichlorophosphate, ethyl dichlorophosphate, diphenyl chlorophosphate, 1,2-phenylene phosphochloridate, phenyl dichlorophosphate, and compounds represented by following Formula (1b-1):

[Chem. 9]

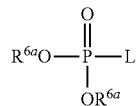

(1b-1)

wherein $R^{6a}$ represents methyl group, ethyl group or phenyl group; and L is as defined above.

Specific examples of the phosphine compounds represented by Formula (1c) include halophosphine derivatives such as chlorodimethylphosphine, chlorodiethylphosphine, chlorodipropylphosphine, chlorodiphenylphosphine, dichloroethylphosphine, dichlorobutylphosphine and dichlorohexylphosphine; and compounds represented by following Formula (1c-1):

[Chem. 10]

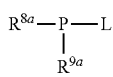

(1c-1)

wherein $R^{8a}$ and $R^{9a}$ each represent methyl group, ethyl group or phenyl group; and L is as defined above.

Specific examples of the imide compounds represented by Formula (1d) include succinimide derivatives including N-halosuccinimide derivatives such as N-chlorosuccinimide, N-bromosuccinimide, N-iodosuccinimide and N-fluorosuccinimide; phthalimide derivatives including N-halophthalimide derivatives such as N-chlorophthalimide, N-bromophthalimide, N-iodophthalimide and N-fluorophthalimide; maleimide derivatives including N-halomaleimide derivatives such as N-chloromaleimide, N-bromomaleimide, N-iodomaleimide and N-fluoromaleimide; isocyanuric acid derivatives including isocyanuric halide derivatives such as trichloroisocyanuric acid (isocyanuric chloride) and sodium dichloroisocyanurate; and hydantoin derivatives including halohydantoin derivatives such as 1,3-dichloro-5,5-dimethylhydantoin and 1,3-dibromo-5,5-dimethylhydantoin.

Specific examples of the sulfonyl or sulfinyl compounds represented by Formula (1e) include sulfonyl halide derivatives such as methanesulfonyl chloride, ethanesulfonyl chloride, propanesulfonyl chloride, trichloromethanesulfonyl chloride, trifluoromethanesulfonyl chloride, benzenesulfonyl chloride, toluenesulfonyl chloride, nitrobenzenesulfonyl chloride, chlorobenzenesulfonyl chloride, fluorobenzenesulfonyl chloride and naphthalenesulfonyl chloride; sulfaryl chloride; and thionyl chloride.

Specific examples of the silane compounds represented by Formula (1f) include halosilane derivatives such as chlorotriphenylsilane, dichlorodiphenylsilane and phenyltrichlorosilane.

Specific examples of the cyclic compounds represented by Formula (1g) and containing silicon atoms as ring constituents include a compound represented by following Formula (1g-1):

[Chem. 11]

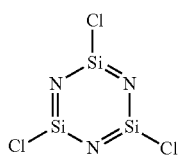

(1g-1)

Of these, phosphazene compounds represented by Formula (1a), phosphoric ester compounds represented by Formula (1b), and imide compounds represented by Formula (1d) are advantageously usable.

When the compound (A2) containing one or more structures represented by Formula (1) is a compound having an —OR' group as $L^A$, the compound may be previously prepared before being subjected to the reaction, but such compound having an —OR' group as $L^A$ can also be formed by incorporating a corresponding compound having a halogen atom as $L^A$ and a compound capable of generating an R'O⁻ ion into the reaction system for producing the amide or lactam, to allow a substitution reaction between the halogen atom and the —OR' group to proceed within the reaction system. Though not especially limited, the compound capable of generating an R'O⁻ ion is often a fluorine-containing alcohol used as a promoter mentioned later, or an oxime compound used as the raw material. Specifically, embodiments of the present invention in which $L^A$ is an —OR' group include an embodiment in which a compound containing one or more structures represented by Formula (1) wherein $L^A$ is a halogen atom is used, and this compound is allowed to react with a fluorine-containing alcohol in the reaction system to give a compound having a haloalkoxy group as a substituent; and an embodiment in which the used compound is allowed to react with an oxime compound in the reaction system to give a compound having, as a substituent, a group which corresponds to the oxime compound, except for removing a hydrogen atom therefrom (e.g., a cycloalkylideneaminooxy group).

The compound (A2) containing one or more structures represented by Formula (1) shows a high catalytic activity in a Beckman rearrangement reaction, as with the aromatic compound (A1). Though its mechanism remaining unknown, this is probably because the rearrangement reaction proceeds through an intermediate in which oxygen atom in the oxime moiety of the substrate oxime compound is bound to the heteroatom Z (P, N, S, B, or Si atom) in the compound containing one or more structures represented by Formula (1), and in this stage, the leaving group $L^A$ in Formula (1) is bound to a proton in the oxime moiety of the oxime compound and leaves as $L^A$-H.

Each of different aromatic compounds (A1) and each of different compounds (A2) containing one or more structures represented by Formula (1) can be used alone or in combination, respectively. The amount (total amount) of at least one catalyst selected from the group consisting of the aromatic compounds (A1) and compounds (A2) containing one or more structures represented by Formula (1) is typically about 0.0001 to about 1 mole, preferably about 0.0005 to about 0.5 mole, and more preferably about 0.001 to about 0.2 mole, per 1 mole of the oxime compound.

[Co-Catalyst]

The production process according to the present invention employs a halogen-containing organic acid as a co-catalyst. The use of a halogen-containing organic acid as a co-catalyst allows the reaction to proceed smoothly even when a nonpolar solvent or low-polarity solvent is used as a reaction solvent. This in turn allows easy separation between a reaction product and the catalysts through an extraction operation with water, after the completion of the reaction.

Exemplary halogen-containing organic acids include halogen-containing organic acids having 1 to about 6 carbon atoms, including halogen-containing carboxylic acids such as monochloroacetic acid, dichloroacetic acid, trichloroacetic acid and trifluoroacetic acid; and halogen-containing sulfonic acids such as trichloromethanesulfonic acid and trifluoromethanesulfonic acid. Of these, preferred are fluorine-containing carboxylic acids such as trifluoroacetic acid, and fluorine-containing sulfonic acids such as trifluoromethanesulfonic acid, of which fluorine-containing carboxylic acids such as trifluoroacetic acid are more preferred.

Each of different halogen-containing organic acids can be used alone or in combination. Such halogen-containing organic acids as the co-catalyst are used in an amount (total amount) of typically 0.1 mole or more (e.g., about 0.1 to about 100 mole), preferably 1 mole or more (e.g., about 1 to about 50 mole), and more preferably 2 moles or more (e.g., about 2 to about 30 moles), per 1 mole of the raw material oxime compound. The halogen-containing organic acids can be used in large excess to the oxime compound.

[Solvents]

The rearrangement reaction of the oxime compound is performed in the presence of a solvent. The solvent is not specifically limited, as long as being inert (inactive) under reaction conditions, but compounds corresponding to the catalysts and co-catalysts are excluded. Examples of such solvents include alkane acids such as acetic acid and propionic acid; nitriles such as acetonitrile, propionitrile and benzonitrile; amides such as formamide, acetamide, dimethylformamide (DMF) and dimethylacetamide; nitro compounds such as nitrobenzene, nitromethane and nitroethane; esters such as ethyl acetate and butyl acetate; fluorine-containing alcohols (mentioned later) such as hexafluoroisopropyl alcohol and trifluoroethanol; hydrocarbons (hydrocarbon solvents) including aliphatic hydrocarbons such as pentane, hexane, heptane, octane, decane and dodecane, alicyclic hydrocarbons such as cyclopentane, cyclohexane, cyclooctane, cyclodecane, cyclododecane and cyclopentadecane, and aromatic hydrocarbons such as benzene, toluene, xylenes, ethylbenzene, and mesitylene; ethers (ether solvents) including chain ethers such as dipropyl ether, diisopropyl ether, dibutyl ether and dihexyl ether, and cyclic ethers such as tetrahydrofuran and dioxane; halogenated hydrocarbons (halogenated hydrocarbon solvents) such as methylene chloride, dichloroethane, chloroform, carbon tetrachloride, chlorobenzene and trifluoromethylbenzene; and ketones (ketone solvents) such as acetone, methyl ethyl ketone, diethyl ketone, diisobutyl ketone and cyclohexanone. Each of such solvents can be used alone or in combination as a mixture. When the aromatic compound(s) (A1) alone is used as the catalyst, at least one solvent selected from the group consisting of hydrocarbon solvents, ether solvents, halogenated hydrocarbon solvents and ketone solvents is used. Among them, the solvent in this case is preferably at least one solvent selected from the group consisting of hydrocarbon solvents, ether solvents and ketone solvents.

The production process according to the present invention allows the catalyst to exhibit a high catalytic activity and allows the reaction to proceed smoothly even when performing the reaction in a nonpolar solvent (e.g., a hydrocarbon solvent) or a solvent having relatively low polarity (e.g., an ether solvent, halogenated hydrocarbon solvent or ketone solvent). The process thereby does not need to use a polar solvent, and this allows easy separation between a reaction product and the used catalysts typically through an extraction operation with water after the completion of the reaction. The process can thereby produce corresponding amides or lactams from oxime compounds industrially efficiently at low cost.

When a chain or cyclic oxime compound represented by Formula (4) or Formula (5) mentioned later is used as the raw material oxime compound, it is also preferred to use, as the solvent, a corresponding substituted or unsubstituted alkane or (m+1)-membered cycloalkane (hereinafter simply referred to as an "alkane or cycloalkane") [e.g., a compound represented by Formula (9) or Formula (10) mentioned later]. This is because as follows. The oxime compound represented by Formula (4) or Formula (5) can be prepared by a process of oxidizing a corresponding alkane or cycloalkane to a corresponding chain or cyclic ketone, and allowing this to react with hydroxylamine; or a process of allowing a corresponding alkane or cycloalkane to react with a nitrous ester or nitrite salt (nitrous acid salt). When an oxime compound represented by Formula (4) or Formula (5) is subjected to a rearrangement reaction in the present invention, the use of an alkane or cycloalkane corresponding to the oxime compound represented by Formula (4) or Formula (5) as the solvent allows the use of a residual alkane or cycloalkane remaining unreacted in an upstream step (precedent step) as the solvent. This eliminates the need of separating a reaction product from the unreacted raw material (alkane or cycloalkane) in the upstream step, and the reaction mixture obtained in the upstream step can be subjected to this step without any treatment or with a simple treatment (e.g., separation of the catalyst through extraction), thus being very advantageous both in view of energy and in view of process. The oxidation reaction of the alkane or cycloalkane, the oximation reaction of the chain or cyclic ketone, and the reaction between the alkane or cycloalkane and the nitrous ester or nitrite salt can each be performed according to known procedures.

The solvent herein is used in an amount of typically about 0.1 to about 50 times by weight, preferably about 0.5 to about 20 times by weight, and more preferably about 1 to about 10 times by weight, relative to the raw material oxime compound. The solvent, if used in an excessively small amount, may often cause the target compound (Amide or lactam) to be produced in a lower yield. In contrast, the solvent, if used in an excessively large amount, may lower the reaction rate to increase the catalyst amount, thus being inefficient.

[Oxime Compounds]

The oxime compound for use as a raw material in the present invention is not especially limited and can be appropriately chosen corresponding to an amide or lactam to be produced. Exemplary oxime compounds include compounds represented by following Formula (4) or Formula (5):

[Chem. 12]

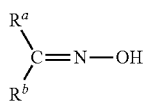

(4)

wherein $R^a$ and $R^b$ each independently represent an organic group, wherein one of $R^a$ and $R^b$ may be a hydrogen atom;

[Chem. 13]

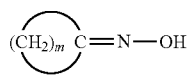

(5)

wherein "m" denotes an integer of 2 or more.

Exemplary organic groups as $R^a$ and $R^b$ include alkyl groups such as methyl, ethyl, propyl, isopropyl, butyl, isobutyl, s-butyl, t-butyl, pentyl, isopentyl, hexyl, isohexyl, heptyl, octyl, nonyl, decyl, dodecyl and pentadecyl groups (e.g., alkyl groups having 1 to 20 carbon atoms, of which alkyl groups having 1 to 12 carbon atoms are preferred, and alkyl groups having 2 to 8 carbon atoms are more preferred); alkenyl groups such as vinyl, allyl, 1-propenyl, 1-butenyl, 1-pentenyl and 1-octenyl groups (e.g., alkenyl groups having 2 to 20 carbon atoms, of which alkenyl groups having 2 to 12 carbon atoms are preferred, and alkenyl group having 2 to 8 carbon atoms are more preferred); alkynyl groups such as ethynyl and 1-propynyl groups (e.g., alkynyl groups having 2 to 20 carbon atoms, of which alkynyl groups having 2 to 12 carbon atoms are preferred, and alkynyl groups having 2 to 8 carbon atoms are more preferred); cycloalkyl groups such as cyclopropyl, cyclobutyl, cyclopentyl, cyclohexyl, cycloheptyl, cyclooctyl and cyclododecyl groups (e.g., cycloalkyl groups having 3 to 20 carbon atoms, of which cycloalkyl groups having 3 to 15 carbon atoms are preferred); cycloalkenyl groups such as cyclopentenyl, cyclohexenyl and cyclooctenyl groups (e.g., cycloalkenyl groups having 3 to 20 carbon atoms, of which cycloalkenyl groups having 3 to 15 carbon atoms are preferred); aryl groups such as phenyl and naphthyl groups; aralkyl groups such as benzyl, 2-phenylethyl and 3-phenylpropyl groups; and aromatic or nonaromatic heterocyclic groups such as 2-pyridyl, 2-quinolyl, 2-furyl, 2-thienyl and 4-piperidinyl groups. These organic group may each have various substituents within ranges not adversely affecting the reaction. Examples of such substituents include halogen atoms, oxo group, hydroxyl group, mercapto group, substituted oxy groups (e.g., alkoxy groups, aryloxy groups and acyloxy groups), substituted thio groups, carboxyl group, substituted oxycarbonyl groups, substituted or unsubstituted carbamoyl groups, cyano group, nitro group, substituted or unsubstituted amino groups, alkyl groups, alkenyl groups, alkynyl groups, cycloalkyl groups, cycloalkenyl groups, aryl groups (e.g., phenyl and naphthyl groups), aralkyl groups and heterocyclic groups.

Specific examples of the oxime compounds represented by Formula (4) include acetaldehyde oxime, acetone oxime, 2-butanone oxime, 2-pentanone oxime, 3-pentanone oxime, 1 cyclohexyl-1-propanone oxime, benzaldehyde oxime, acetophenone oxime, benzophenone oxime and 4'-hydroxyacetophenone oxime.

In Formula (5), the ring may have one or more substituents bound thereto and may have one or more other rings fused therewith. The number "m" is typically about 2 to about 30, preferably about 4 to about 20, and more preferably about 5 to about 14. Exemplary cyclic oxime compounds represented by Formula (5) include cyclopropanone oxime, cyclobutanone oxime, cyclohexanone oxime, cycloheptanone oxime, cyclooctanone oxime, cyclononanone oxime, cyclodecanone oxime, cyclododecanone oxime, cyclotridecanone oxime, cyclotetradecanone oxime, cyclopentadecanone oxime, cyclohexadecanone oxime, cyclooctadecanone oxime and cyclononadecanone oxime. Exemplary substituents which may be bound to the ring are as with the substituents which the organic group may have.

Ones of preferred embodiments of the present invention include an embodiment in which the oxime compound is an oxime compound represented by Formula (4), $L^A$ in Formula (1) is an —OR' group, and R' is a group represented by following Formula (4a); and an embodiment in which the oxime compound is an oxime compound represented by Formula (5), $L^A$ in Formula (1) is an —OR' group, and R' is a group represented by following Formula (5a):

[Chem. 14]

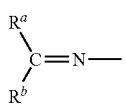

(4a)

wherein $R^a$ and $R^b$ each represent an organic group, and wherein one of $R^a$ and $R^b$ may be a hydrogen atom;

[Chem. 15]

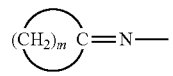

(5a)

wherein "m" denotes an integer of 2 or more.

Each of different oxime compounds may be chosen and used alone or in combination.

[Rearrangement Reactions]

The rearrangement reaction of the oxime compound can be performed at a reaction temperature which is not critical and can be chosen as appropriate according typically to the type of the oxime compound, and the types of other components such as the catalyst, co-catalyst and solvent. The reaction temperature is typically about 0° C. to about 250° C., preferably about 25° C. to about 150° C., and more preferably about 40° C. to about 120° C. The reaction can be performed in an atmosphere of an inert gas such as nitrogen or argon or can be performed in an air atmosphere or in an oxygen atmosphere. The reaction herein can be preferably performed in an air atmosphere under reflux conditions.

The catalyst in this reaction may show a significantly improved catalytic activity when a fluorine-containing alcohol is used as a solvent or an additive agent (promoter). The fluorine-containing alcohol is not limited and can be any of aliphatic alcohols and aromatic alcohols, except with part or all of hydrogen atoms of the hydrocarbon moiety being substituted with fluorine atoms. The fluorine-containing alcohol may be a monohydric alcohol or polyhydric alcohol.

The fluorine-containing aliphatic alcohols include aliphatic chain alcohols and aliphatic cyclic (alicyclic) alcohols. Preferred examples of aliphatic chain alcohols usable herein include fluorine-containing straight-chain aliphatic alcohols corresponding to straight-chain alcohols having 1 to about 20 carbon atoms, except with part or all of hydrogen atoms of the hydrocarbon moiety being substituted with fluorine atoms; and fluorine-containing branched-chain aliphatic alcohols corresponding to branched-chain alcohols having 3 to about 20 carbon atoms, except with part or all of hydrogen atoms of the hydrocarbon moiety being substituted with fluorine atoms. The hydrocarbon moieties (or fluorinated hydrocarbon moieties) in the fluorine-containing aliphatic chain alcohols may each contain one or more unsaturated bonds. Specific examples of such fluorine-containing straight-chain aliphatic alcohols, part of hydrogens of whose hydrocarbon moiety being substituted with fluorine atoms, include 1,1-difluoroethanol, 1,1,2-trifluoroethanol, 2,2,2-trifluoroethanol, 1,1-difluoro-1-propanol, 1,2-difluoro-1-propanol, 1,2,3-trifluoro-1-propanol, 3,3,3-trifluoro-1-propanol, 1,1,2,2-tetrafluoro-1-propanol, 1,3-difluoro-1,3-propanediol, 2,3,4-trifluoro-1-butanol, 4,4,4-trifluoro-1-butanol, 3,3,4,4-pentafluoro-1-butanol, 1,1,2,2,3,3-hexafluoro-1-butanol, 1,1,2,2-tetrafluoro-1-butanol, 1,2,3,4-tetrafluoro-1-butanol, 3,3,4,4,4-pentafluoro-1-butanol, 1,2,3,4-tetrafluoro-1,4-butanediol, 1,1,2,2-tetrafluoro-1-pentanol, 5,5,5-trifluoro-1-pentanol, 4,4,5,5,5-pentafluoro-1-pentanol, 1,1,2,2-tetrafluoro-1-hexanol and 5,5,6,6,6-pentafluoro-1-hexanol. Exemplary fluorine-containing branched-chain aliphatic alcohols include hexafluoroisopropyl alcohol, heptafluoroisopropyl alcohol, 3,3,3-trifluoro-2-trifluoromethyl-1-propanol, 2-trifluoromethyl-1-butanol, 2-trifluoromethyl-1,4-butanediol and 2-trifluoromethyl-3,3,4,4,4-pentafluoro-1-butanol.

Exemplary fluorine-containing aliphatic cyclic alcohols usable herein include alicyclic alcohols having 3 to about 20 carbon atoms, such as cyclohexanol and cyclopentanol, except for containing one or more fluorine atoms per molecule. The fluorine-containing aliphatic cyclic alcohols may contain one or more fluorine atoms in any form. For example, the fluorine-containing aliphatic cyclic alcohols may contain fluorine atom(s) as being bound to carbon atom(s) constituting the ring or as being contained in a hydrocarbon group that is bound to carbon atom(s) constituting the ring.

Exemplary fluorine-containing aromatic alcohols usable herein include aromatic alcohols, such as benzyl alcohol and phenylethanol, except for containing one or more fluorine atoms per molecule. The fluorine-containing aromatic alcohols may contain fluorine atom(s) in any form. For example, the fluorine-containing aromatic alcohols may contain a fluorinated hydrocarbon group substituted on the aromatic ring or may contain fluorine atom(s) in a chain hydrocarbon moiety thereof.

The catalyst in this reaction may show a significantly improved catalytic activity when an acid (other than halogen-containing organic acids) is added. The acid may be any of Lewis acids and Broensted acids. Exemplary Lewis acids include aluminum chloride, zinc chloride and metal triflates. Exemplary Broensted acids include inorganic acids such as sulfuric acid, hydrochloric acid and nitric acid; and organic acids including sulfonic acids such as p-toluenesulfonic acid and methanesulfonic acid.

The acid is used in an amount of typically about 0.0001 to about 1 mole, preferably about 0.0005 to about 0.5 mole, and more preferably about 0.001 to about 0.2 mole, per 1 mole of the oxime compound. Each of different acids can be used alone or in combination.

When reacted according to the process of the present invention, for example, an oxime compound represented by Formula (4) gives an amide compound represented by following Formula (6); and a cyclic oxime compound represented by Formula (5) gives a lactam represented by following Formula (7). More specifically, acetophenone oxime gives, for example, acetanilide; and a cycloalkanone oxime gives a corresponding lactam having one more member than the cycloalkanone. Typically, cyclohexanone oxime gives ε-caprolactam; cycloheptanone oxime gives 7-heptane lactam; cyclooctanone oxime gives 8-octane lactam; and cyclododecanone oxime gives 12-laurolactam. The groups $R^a$ and $R^b$ in Formula (6) and the repetition number "m" in Formula (7) are as defined above.

[Chem. 16]

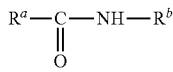

(6)

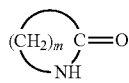

(7)

After the completion of the reaction, a reaction product can be separated and purified through a separation procedure such as filtration, concentration, distillation, extraction, crystallization, recrystallization, adsorption or column chromatography, or any combination of them.

[Preparation of Oxime Compounds]

The oxime compound is very advantageously prepared by a process mentioned below, because it can be efficiently prepared simply under mild conditions; and, additionally, the reaction for synthesizing an oxime compound, and the reaction for producing an amide or lactam through rearrangement of the oxime compound can be carried out in one step without requiring an extra intermediate step for separating and purifying the oxime compound.

Specifically, the oxime compound is preferably prepared while allowing a compound having a methyl group or methylene group to react with a nitrous ester or nitrite salt in the presence of a nitrogen-containing cyclic compound containing, as a ring constituent, a skeleton represented by following Formula (8):

[Chem. 18]

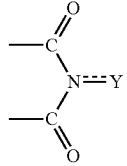

(8)

wherein Y represents an oxygen atom or an —OR" group, and wherein R" represents a hydrogen atom or a hydroxyl-protecting group.

Specific usable examples of the nitrogen-containing cyclic compound having a skeleton represented by Formula (8) as a ring constituent include N-hydroxy imide compounds derived from aliphatic polycarboxylic acid anhydrides (cyclic anhydrides) or aromatic polycarboxylic acid anhydrides (cyclic anhydrides), such as N-hydroxysuccinimide, N-hydroxyphthalimide, N,N'-dihydroxypyromellitic diimide, N-hydroxyglutarimide, N-hydroxy-1,8-naphthalenedicarboximide, and N,N'-dihydroxy-1,8,4,5-naphthalenetetracarboxylic diimide; and compounds corresponding to the N-hydroxy imide compounds, except with hydroxyl group(s) each being protected by a protecting group (e.g., an acyl group such as acetyl group).

Examples of the compound having a methyl group or methylene group include compounds represented by following Formula (9):

[Chem. 19]

$$R^a\text{—}CH_2\text{—}R^b \qquad (9)$$

wherein $R^a$ and $R^b$ are as defined above.

Specific examples of the above compounds include ethane, propane, butane, pentane, hexane, heptane, octane, n-propylcyclohexane, toluene, p-xylene, ethylbenzene, isopropylbenzene, diphenylmethane and 1,2-diphenylethane.

Exemplary compounds having a methylene group further include compounds represented by following Formula (10):

[Chem. 20]

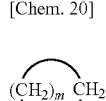

(10)

wherein "m" is as defined above.

The ring in Formula (10) may have one or more substituents bound thereto and/or may have one or more other rings fused therewith. Exemplary compounds represented by Formula (10) include cyclopropane, cyclobutane, cyclopentane, cyclohexane, cycloheptane, cyclooctane, cyclononane, cyclodecane, cyclododecane, cyclotridecane, cyclotetradecane, cyclopentadecane, cyclohexadecane, cyclooctadecane and cyclononadecane. Exemplary substituents which may be bound to the ring are as with the substituents which the organic group may have.

Exemplary nitrous esters include alkyl nitrites such as methyl nitrite, ethyl nitrite, propyl nitrite, isopropyl nitrite, butyl nitrite, isobutyl nitrite, t-butyl nitrite, amyl nitrite, isoamyl nitrite, t-amyl nitrite, and hexyl nitrite; aryl nitrites such as phenyl nitrite; and aralkyl nitrites such as benzyl nitrite. Preferred examples of nitrous esters include alkyl nitrites such as alkyl nitrites whose alkyl moiety having 1 to 6 carbon atoms. Exemplary nitrite salts include ammonium nitrite; nitrites of alkaline earth metals, such as lithium nitrite, sodium nitrite, potassium nitrite and barium nitrite; and nitrites of other metals, such as zinc nitrite.

The compound having a methyl group or methylene group and the nitrous ester or nitrite salt can be used in proportions which can be chosen as appropriate according typically to the types and combination of the two compounds. For example, the compound having a methyl group or methylene group may be used in an amount substantially equivalent or in excess (e.g., about 1.1 to about 50 times by equivalent or more, and preferably about 3 to about 30 times by equivalent) to the nitrous ester or nitrite salt; or contrarily, the nitrous ester or nitrite salt may be used in excess to the compound having a methyl group or methylene group.

The reaction between the compound having a methyl group or methylene group and the nitrous ester or nitrite salt is performed in the presence of, or in the absence of, a solvent. The solvent is not especially limited and can be, for example, any of the solvents usable in the rearrangement reaction of the oxime compound. The reaction temperature and other conditions are not especially limited, and the reaction herein can be carried out typically under the same or similar conditions to those in the rearrangement reaction of the oxime compound. Typically, the reaction temperature is about 0° C. to about 250° C., preferably about 25° C. to about 150° C., and more preferably about 40° C. to about 120° C. The reaction may be carried out in an atmosphere of an inert gas such as nitrogen or argon gas, but it can be carried out in an air atmosphere or oxygen atmosphere typically in the case of target products of some types. The reaction can be carried out under reduced pressure, under normal atmospheric pressure, or under a pressure (under a load), according to a common system or procedure such as a batch system, semi-batch system, or continuous system (e.g., multistage continuous circulation system). The yield is significantly improved when the reaction is carried out under reduced pressure, especially under such a reduced pressure that nitrogen oxide gases (particularly $NO_2$) produced as by-products through the reaction can be removed from the system [e.g., about 30 to about 700 mmHg (About 3.99 to about 93.1 kPa)]. This is probably because nitrogen oxide gases such as $NO_2$ will inhibit the reaction.

It is conceivable that the reaction between the compound having a methyl group or methylene group and the nitrous ester or nitrite salt may initially give a nitroso compound, and this compound may be rearranged to give an oxime compound. For example, it is conceivable that the reaction between cyclohexane and a nitrous ester or nitrite salt may initially give nitrosocyclohexane, and this compound may be rearranged to give cyclohexanone oxime. Though varying from type to type, a nitroso compound of some type may be in reversible equilibrium with a corresponding dimer (di-N-oxide compound in which two molecules of the nitroso compound are bound through their nitrogen atoms), and the equilibrium may lie to the dimer. When the reaction is carried out over a long period of time, the nitroso compound and a dimer thereof can be in a trace amount, at most in a yield of less than 1%.

In a preferred embodiment, the reaction between the compound having a methyl group or methylene group and the nitrous ester or nitrite salt is carried out while sequentially or continuously adding the nitrous ester or nitrite salt to the reaction system. According to this technique, side reactions particularly in the nitrosation stage can be suppressed, to yield the nitroso compound (or a dimer thereof) with a high selectivity, as compared to a technique of adding the nitrous ester or nitrite salt at once. Thus, an oxime compound, for example, can be obtained in a high yield typically through a subsequent rearrangement reaction.

In another embodiment for producing an oxime compound in a good yield, reactions are allowed to proceed stepwise by independently providing the step of reacting a compound having a methyl group or methylene group with a nitrous ester or nitrite salt to give a nitroso compound or a dimer thereof and the step of converting the resulting nitroso compound or dimer thereof into an oxime compound. In this embodiment, the total reaction time can be significantly shortened by adding an additive agent to the reaction system or carrying out heating in the subsequent conversion step (rearrangement step of the nitroso compound). The subsequent rearrangement step may use another solvent than the solvent used in the precedent nitrosation step. In this embodiment, the precedent nitrosation step is preferably carried out under reduced pressure, because this significantly improves the yield for the same reason as above.

Though not especially limited, as long as being capable of inducing the rearrangement from a nitroso form to an oxime form, the additive agent is preferably chosen typically from acids and bases. Exemplary acids herein include sulfonic acids such as methanesulfonic acid, trifluoromethanesulfonic acid, benzenesulfonic acid and p-toluenesulfonic acid; mineral acids such as sulfuric acid, nitric acid, hydrochloric acid, phosphoric acid, boric acid and fuming sulfuric acid; Lewis acids such as aluminum chloride, zinc chloride and scandium triflate; solid acids such as silica, alumina and zeolite; complex acids including polyacids such as phosphomolybdic acid, phosphotungstic acid, silicomolybdic acid and silicotungstic acid; and strongly acidic cation-exchange resins. Exemplary bases include organic bases including tertiary amines such as triethylamine, nitrogen-containing heterocyclic compounds such as pyridine, as well as sodium acetate and sodium methoxide; inorganic bases such as sodium carbonate, sodium hydrogen carbonate, sodium hydroxide and potassium hydroxide; and solid bases such as magnesium oxide, hydrotalcite and hydroxyapatite. The additive agent(s) may be added at once or in two or more installments. The amount of additive agent(s) is typically about 0.01 to about 100 parts by weight, preferably about 0.1 to about 50 parts by weight, and more preferably about 0.3 to about 30 parts by weight, per 100 parts by weight of the compound having a methyl group or methylene group. A rearrangement reaction using additive agents may be carried out at a temperature of typically about 40° C. to about 120° C. and preferably about 50° C. to about 100° C. for a duration of typically about 5 to about 180 minutes, and preferably about 10 to about 120 minutes. A rearrangement reaction with heating may be carried out at a heating temperature of typically about 120° C. to about 250° C. and preferably about 150° C. to about 200° C. for a reaction time of typically about 0.5 to about 120 minutes and preferably about 2 to about 90 minutes.

In the production of an oxime compound, it is possible to produce a corresponding amide or lactam from a compound having a methyl group or methylene group in one step, by simultaneously adding the catalyst and the co-catalyst in addition to the compound having a methyl group or methylene group, the nitrous ester or nitrite salt and the nitrogen-containing cyclic compound having a skeleton represented by Formula (8) as a ring constituent and carrying out a reaction. In another possible process, a reaction between the compound having a methyl group or methylene group and the nitrous ester or nitrite salt is carried out in the presence of the nitrogen-containing cyclic compound having a skeleton represented by Formula (8) as a ring constituent and in the presence of the catalyst to form an oxime compound, and then the co-catalyst is added to perform a rearrangement reaction of the oxime compound. In yet another possible process, a reaction between the compound having a methyl group or methylene group and the nitrous ester or nitrite salt is carried out in the presence of the nitrogen-containing cyclic compound having a skeleton represented by Formula (8) as a ring constituent and in the presence of the co-catalyst to form an oxime compound, and the catalyst is then added to perform a rearrangement reaction of the oxime compound. In still another possible process, a reaction between the compound having a methyl group or methylene group and the nitrous ester or nitrite salt is carried out in the presence of the nitrogen-containing cyclic compound having a skeleton represented by Formula (8) as a ring constituent to form an oxime compound, and the catalyst and the co-catalyst are then added to perform a rearrangement reaction of the oxime compound. In these processes, an operation such as distilling off of the solvent, concentration, or exchange of the solvent may be carried out in an appropriate stage. In a preferred embodiment, the used nitrogen-containing cyclic compound having a skeleton represented by Formula (8) as a ring constituent is removed typically through precipitation and filtration before the Beckmann rearrangement reaction. The production of the oxime compound may be conducted stepwise (step by step), as described above.

According to the process of the present invention, amides or lactams can be produced simply in high yields without causing large amounts of by-products. Further, high-purity amides or lactams cab be produced in a simple manner, because the catalyst and other components for use in the present invention are easily separable from the product amides or lactams. Reaction products after the completion of the reaction can be easily separated from the used catalyst and other components typically through an extraction operation with water, because the reaction can proceed smoothly even when a nonpolar solvent or low-polarity solvent is used. Additionally, amides or lactams can be efficiently produced in a simple manner, because it is possible to carry out the step of producing an oxime from a raw material such as an aliphatic or aromatic hydrocarbon and the step of producing an amide or lactam form the oxime compound as one step or in one pot. Typically, ε-caprolactam and ω-laurolactam can be efficiently produced from cyclohexane and cyclododecane, respectively.

The product amides or lactams are very industrially important, because they can be used typically as raw materials for pharmaceutical drugs, agricultural chemicals, dyestuffs, solvents, and explosives; and as raw materials for polyamides (nylons).

EXAMPLES

The present invention will be illustrated in further detail with reference to several working examples below. It should be noted, however, that these examples are never construed to limit the scope of the present invention.

Comparative Example 1

Cyclohexanone oxime (10 mmol), hexachlorophosphazene [compound of Formula (1a) in which $L^A$, $R^1$, $R^2$, $R^3$, $R^4$ and $R^5$ are each chlorine (Cl); 1 mmol] and toluene (20 mL) were placed in a reactor, followed by stirring at 70° C. for 2 hours. A gas chromatographic analysis was performed after the reaction to find that ε-caprolactam was formed in a yield of 22%.

Comparative Example 2

Cyclohexanone oxime (10 mmol), hexachlorophosphazene (1 mmol) and trifluoroacetic acid (20 mL) were placed in a reactor, followed by stirring at 70° C. for 2 hours. A gas chromatographic analysis was performed after the reaction to find that ε-caprolactam was formed in a yield of 19%.

Example 1

Cyclohexanone oxime (10 mmol), hexachlorophosphazene (1 mmol), trifluoroacetic acid (12 mL) and toluene (8 mL) were placed in a reactor, followed by stirring at 70° C. for 2 hours. A gas chromatographic analysis was performed after the reaction to find that ε-caprolactam was formed in a yield of 65%.

Example 2

Cyclohexanone oxime (10 mmol), hexachlorophosphazene (1 mmol), trifluoroacetic acid (12 mL) and toluene (10 mL) were placed in a reactor, followed by stirring at 70° C. for 2 hours. A gas chromatographic analysis was performed after the reaction to find that ε-caprolactam was formed in a yield of 58%.

Example 3

Cyclohexanone oxime (10 mmol), hexachlorophosphazene (1 mmol), trifluoroacetic acid (12 mL) and toluene (8 mL) were placed in a reactor, followed by stirring at 70° C. for 4 hours. A gas chromatographic analysis was performed after the reaction to find that ε-caprolactam was formed in a yield of 88%.

Example 4

Cyclohexanone oxime (10 mmol), hexachlorophosphazene (0.5 mmol), trifluoroacetic acid (12 mL) and toluene (8 mL) were placed in a reactor, followed by stirring at 70° C. for 15 hours. A gas chromatographic analysis was performed after the reaction to find that ε-caprolactam was formed in a yield of 81%.

Example 5

Cyclohexanone oxime (10 mmol), 2,4,6-trichloro-1,3,5-triazine (0.5 mmol), trifluoroacetic acid (12 mL) and toluene (8 mL) were placed in a reactor, followed by stirring at 70° C.

for 4 hours. A gas chromatographic analysis was performed after the reaction to find that ε-caprolactam was formed in a yield of 97%.

Example 6

Cyclohexanone oxime (10 mmol), 2,4,6-trichloro-1,3,5-triazine (0.5 mmol), trifluoroacetic acid (12 mL) and toluene (8 mL) were placed in a reactor, followed by stirring at 50° C. for 4 hours. A gas chromatographic analysis was performed after the reaction to find that ε-caprolactam was formed in a yield of 83%.

Example 7

Cyclohexanone oxime (20 mmol), 2,4,6-trichloro-1,3,5-triazine (1 mmol), trifluoroacetic acid (12 mL) and toluene (8 mL) were placed in a reactor, followed by stirring at 70° C. for 4 hours. A gas chromatographic analysis was performed after the reaction to find that ε-caprolactam was formed in a yield of 99%.

Example 8

Cyclohexanone oxime (20 mmol), 2,4,6-trichloro-1,3,5-triazine (1 mmol), trifluoroacetic acid (12 mL) and benzene (8 mL) were placed in a reactor, followed by stirring at 70° C. for 4 hours. A gas chromatographic analysis was performed after the reaction to find that ε-caprolactam was formed in a yield of 94%.

Example 9

Cyclohexanone oxime (20 mmol), 2,4,6-trichloro-1,3,5-triazine (1 mmol), trifluoroacetic acid (12 mL) and dibutyl ether (8 mL) were placed in a reactor, followed by stirring at 70° C. for 4 hours. A gas chromatographic analysis was performed after the reaction to find that ε-caprolactam was formed in a yield of 71%.

Example 10

Cyclohexanone oxime (20 mmol), 2,4,6-trichloro-1,3,5-triazine (1 mmol), trifluoroacetic acid (12 mL) and acetone (8 mL) were placed in a reactor, followed by stirring at 70° C. for 4 hours. A gas chromatographic analysis was performed after the reaction to find that ε-caprolactam was formed in a yield of 82%.

Example 11

Cyclohexanone oxime (20 mmol), 2,4,6-trichloro-1,3,5-triazine (1 mmol), trifluoroacetic acid (12 mL) and cyclohexane (8 mL) were placed in a reactor, followed by stirring at 70° C. for 4 hours. A gas chromatographic analysis was performed after the reaction to find that ε-caprolactam was formed in a yield of 71%.

Example 12

Cyclohexanone oxime (20 mmol), 2,4,6-trihydroxy-1,3,5-triazine (cyanuric acid) (1 mmol), trifluoroacetic acid (12 mL) and toluene (8 mL) were placed in a reactor, followed by stirring at 70° C. for 4 hours. A gas chromatographic analysis was performed after the reaction to find that ε-caprolactam was formed in a yield of 66%.

Example 13

Cyclohexanone oxime (20 mmol), N-chlorosuccinimide (1 mmol), trifluoroacetic acid (12 mL) and toluene (8 mL) were placed in a reactor, followed by stirring at 70° C. for 4 hours. A gas chromatographic analysis was performed after the reaction to find that ε-caprolactam was formed in a yield of 55%.

Example 14

Cyclohexanone oxime (20 mmol), isocyanuric chloride (1 mmol), trifluoroacetic acid (12 mL) and toluene (8 mL) were placed in a reactor, followed by stirring at 70° C. for 4 hours. A gas chromatographic analysis was performed after the reaction to find that ε-caprolactam was formed in a yield of 69%.

Example 15

Cyclohexanone oxime (20 mmol), diethoxyphosphoryl chloride (1 mmol), trifluoroacetic acid (12 mL) and toluene (8 mL) were placed in a reactor, followed by stirring at 70° C. for 4 hours. A gas chromatographic analysis was performed after the reaction to find that ε-caprolactam was formed in a yield of 54%.

INDUSTRIAL APPLICABILITY

The present invention allows industrially efficient and low-cost production of corresponding amides or lactams from oxime compounds. The product amides or lactams are usable typically as raw materials for pharmaceuticals, agricultural chemicals, dyestuffs, and polyamides; and as solvents.

The invention claimed is:
1. A process for producing an amide or a lactam, the process comprising the step of subjecting cyclohexanone oxime to rearrangement in the presence of at least one catalyst and a co-catalyst in a solvent to yield the corresponding amide or lactam, the at least one catalyst being selected from the group consisting of an aromatic compound (A1) and a compound (A2),
wherein the aromatic compound (A1) is a triazine compound represented by Formula (2a):

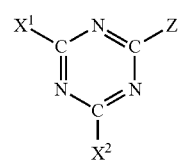

(2a)

wherein Z represents a halogen atom or an —OR group, wherein R represents sulfonyl groups, haloalkyl groups, alkylideneamino groups, or cycloalkylideneamino groups; and $X^1$ and $X^2$ are the same as or different from each other and each represent a hydrogen atom, halogen atom, alkyl group, haloalkyl group, aryl group, cycloalkyl group, hydroxyl group, alkoxy group, aryloxy group, haloalkoxy group, mercapto group, carboxyl group, substituted oxycarbonyl group, formyl group, acyl group, acyloxy group, nitro group, sulfo group, cyano group, amino group, oxyamino group or another organic group, wherein $X^1$ and $X^2$ are optionally bound to each other to form an aromatic or nonaromatic ring with atoms constituting the ring in the formula;

wherein the compound (A2) is selected from the group consisting of phosphazene compounds represented by Formula (1a), phosphoric ester compounds represented by Formula (1b), and imide compounds represented by Formula (1d):

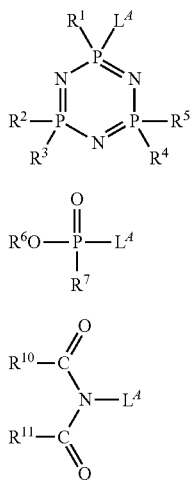

wherein $L^A$ represents a leaving group; $R^1$, $R^2$, $R^3$, $R^4$, $R^5$, $R^6$, $R^7$, $R^{10}$, and $R^{11}$ are the same as or different from one another and each represent a hydrogen atom, halogen atom, alkyl group, haloalkyl group, aryl group, aralkyl group, cycloalkyl group, hydroxyl group, alkoxy group, aryloxy group, haloalkoxy group, mercapto group, carboxyl group, substituted oxycarbonyl group, acyl group, acyloxy group, nitro group, sulfo group, cyano group, amino group, oxyamino group, or another organic group; $R^2$ and $R^3$ are optionally bound to each other to form a ring with the adjacent phosphorus atom; $R^4$ and $R^5$ are optionally bound to each other to form a ring with the adjacent phosphorus atom; $R^6$ and $R^7$ are optionally bound to each other to form a ring with the adjacent oxygen atom and phosphorus atom; $R^{10}$ and $R^{11}$ are optionally bound to each other to form a ring with the adjacent two carbon atoms and nitrogen atom;

wherein the co-catalyst includes a halogen-containing organic acid, wherein, when the aromatic compound (A1) alone is used as the catalyst, the solvent is at least one solvent selected from the group consisting of hydrocarbon solvents, ether solvents, halogenated hydrocarbon solvents and ketone solvents.

2. The process for producing a lactam, according to claim 1, wherein $L^A$ in the compound (A2) is a halogen atom.

\* \* \* \* \*